United States Patent [19]

Levene et al.

[11] Patent Number: 5,107,842
[45] Date of Patent: Apr. 28, 1992

[54] METHOD OF ULTRASOUND IMAGING OF THE GASTROINTESTINAL TRACT

[75] Inventors: Harold B. Levene; Elaine Villapando, both of San Diego; James L. Barnhart, Encinitas; Kenneth J. Widder, Del Mar, all of Calif.

[73] Assignee: Molecular Biosystems, Inc., San Diego, Calif.

[21] Appl. No.: 660,349

[22] Filed: Feb. 22, 1991

[51] Int. Cl.⁵ .............................................. A61B 8/14
[52] U.S. Cl. .............................................. 128/662.02
[58] Field of Search .................. 128/653, 662.02, 672; 73/703, 861.25; 252/311; 424/9

[56] References Cited

U.S. PATENT DOCUMENTS

| | | |
|---|---|---|
| 4,265,251 | 5/1981 | Tickner .......................... 128/662.02 |
| 4,681,119 | 7/1987 | Rasor et al. .................... 128/662.02 |
| 4,957,656 | 9/1990 | Cerny et al. .................... 128/662.02 |

*Primary Examiner*—Francis J. Jaworski
*Assistant Examiner*—George Manuel
*Attorney, Agent, or Firm*—Tilton, Fallon, Lungmus & Chestnut

[57] ABSTRACT

A method is provided for enhanced ultrasonic imaging of the gastrointestinal tract by employing an imaging agent comprising an aqueous particulate dispersion of edible substances, such as insoluble brans and mineral particles. Hydrocolloid particles can also be used, preferably in combination with insoluble non-swelling edible particles.

15 Claims, No Drawings

METHOD OF ULTRASOUND IMAGING OF THE GASTROINTESTINAL TRACT

FIELD OF INVENTION

This invention relates to ultrasonic imaging of the human body for diagnostic purposes; and, more particularly, ultrasonic imaging agents for use in the gastrointestinal tract from the stomach through the large bowel.

BACKGROUND OF INVENTION

An examination procedure known as contrast echocardiography is used clinically to delineate bodily structures. Progress and practical application of ultrasonic imaging has been delayed by the lack of effective clinically usable imaging agents. This is especially the case with respect to ultrasonic imaging agents for the gastrointestinal tract.

Ultrasonic imaging utilizes an ultrasonic scanner to generate and receive sound waves. The scanner is placed on a body surface overlying the area to be imaged, and sound waves are directed toward that area. The scanner detects reflected sound waves and translates that data into images. When ultrasonic energy propagates through an inhomogeneous substance, the acoustic properties of the substance determine the degree of absorption, scattering, and transmission of the ultrasound. As ultrasound waves propagate through one medium to another, there is some degree of reflection at the interface. The degree of reflection is determined by the acoustic properties of each medium; these properties are reflected by the medium density and the speed of sound transmission through the medium. Consequently, changes in the composition of the inhomogeneous substance can change the degree of ultrasonic reflection from the substance.

Contrast agents for diagnostic ultrasound were reviewed by Ophir and Parker, *Ultrasound in Med. & Biol.* (1989), 15:319-333. Various contrast agents are described for intravascular administration and imaging. These included free and encapsulated gas bubbles, colloidal suspensions, emulsions, and aqueous solutions. Different mechanisms which can enhance image contrast are discussed; namely, backscatter contrast, attenuation contrast, and speed of sound contrast. Orally administrable ultrasound contrast agents are not discussed. With respect to the development of parenteral imaging agents, the authors observed that the development "has been slow and sporadic, and to date there are no completely satisfactory materials for clinical imaging." In the concluding paragraph, the authors added: "The clinical need for ultrasound contrast agents is high, but much interdisciplinary research, covering acoustic material properties, imaging, biochemistry, histology, toxicology and related specialties will be required before ultrasound contrast agents are commercially available and in routine clinical use."

Particulate suspensions have been used as vascular contrast agents in radiography. For this purpose, radiopaque particles are employed. A particulate contrast agent for ultrasound imaging for the liver was suggested by Parker et al., *Ultrasound in Med. & Biol.* (1987), 13:555-566. The agent proposed for intravenous injection consisted of an iodipamide ethyl ester in the form of dense, relatively incompressible solid collagen particles. A theoretical description of backscatter versus particle size is found in Morse and Ingard, "Theoretical Acoustics", 1986, (Princeton University Press, Princeton, N.J.). It was proposed that such particles might enhance the ultrasound image by relative motion attenuation and/or backscatter attenuation.

SUMMARY OF INVENTION

This invention provides a method and imaging agents for ultrasonic imaging of the gastrointestinal tract from the stomach to the rectum, hereinafter collectively referred to as the gastrointestinal (GI) tract. The invention is based in part on the unexpected discovery that certain classes of edible particulates, such as insoluble bran particles, hydrocolloid particles, and combinations thereof can be employed to effectively enhance contrast of ultrasonic images of the GI tract. Other particulates and combinations thereof are disclosed in the following more detailed specification.

It is believed that the primary effect of the edible particulate dispersions used in the method of this invention is that they cause backscatter. This backscatter enhancement occurs at ultrasonic beam frequencies commonly employed for examining the body. Some additional enhancement may be obtained due to attenuation of the sound waves by relative motion of the particles. A secondary effect of the invention is the ability of the contrast material to displace gas within the GI tract, such gas causing attenuation and inability to view distal anatomic structures.

DETAILED DESCRIPTION

The ultrasound imaging agents of this invention for use in the gastrointestinal (GI) tract comprise aqueous dispersions of particulate solids. The dispersions may contain from 0.5% to 10% by weight of the particulate solids sized in the range from 1 to 500 microns. These solid particles may be composed principally of insoluble bran particles or other fibrous vegetable particles, or hydrocolloid particles, or preferably mixtures of fibrous vegetable particles with hydrocolloid particles.

Various insoluble cereal grain brans in finely divided condition can be used, including corn bran, oat bran, rice bran, wheat bran, or mixtures of such brans, or other fibrous vegetable particles such as particulate insoluble cellulose. Bran or other vegetable substances which are in a water soluble form are not desirable, since they can dissolve in the aqueous carrier and lose effectiveness for backscatter enhancement.

Instead of bran or cellulose particles, other dense fine food particles can be used, such as particles of wheat germ, wheat grass, dried whey, precipitated casein, and the like. If whey is employed, it is preferable to employ whey of enhanced protein content, since the lactose component of the whey may dissolve in the aqueous carrier. Edible insoluble mineral particles can also be used, such as particulate limestone, dolomite, kaolin or bentonite.

The contrast medium preferably includes hydrocolloids in particulate form, which are preferably not fully swollen to a condition of gelling. However, the hydrocolloid particles can be partially swollen, thereby acting as suspending or dispersing agents with respect to themselves and also with respect to insoluble particles such as bran or whey. Natural hydrocolloids are a preferred sub-class of hydrocolloids. Such hydrocolloids include gum ghatti, gum guar, locust bean gum, tragacanth gum, xanthan gum, arabic gum, pectin, carageenen, agar, modified celluloses, and the like. These natural hydrocolloids in particulate form may be used separately or in combination.

In preferred combinations, non-swelling insoluble vegetable or insoluble mineral particles are used in admixture with partially swollen hydrocolloid particles. The hydrocolloid particles are preferably in the form of discrete partially hydrated particles. For example, from 2 to 6% of insoluble fibrous vegetable particles, insoluble mineral particles, or mixtures thereof may be combined with from about 0.5 to 4% hydrocolloid particles, such as natural gums. The total solids content of the dispersions can be as previously described, viz. 0.5 to 10% by weight and preferably 2 to 8%.

The aqueous particulate dispersions are preferably in a form in which the dispersed particles remain in suspension for sufficient time to carry out the administration of the imaging agent. The particles may be redispersed by agitation of the dispersions, such as by hand shaking, prior to administration.

In addition to the ingredients referred to above, the dispersions may contain other ingredients to improve patentability. For example, the dispersions may contain sweetening agents and/or flavoring agents. Additionally, other ingredients may be added to enhance the degassing effect. An example is surface active agents such as simethicone.

For introduction into the GI tract, whether orally or anally, it is preferred that the suspensions be in sterile form. For example, after preparation, the dispersions can be subjected to heat sterilization. Sterilization procedures should be avoided which tend to agglomerate the particles.

In the preferred embodiments, the imaging dispersions contain from 2 to 8% of the particulate solids. For example, the dispersions may contain from 2 to 6% by weight of bran particles together with from 0.5 to 4% hydrocolloid particles. The dispersion should contain a total of not over 10% solids and perferably not over 8%.

The preparations may be administered orally by the patient drinking a prescribed quantity of the dispersion. Alternatively, the suspension can be administered by rectal enema. The amounts to be administered will depend on the imaging purpose, but, in general, the amounts will range from 100 to 1000 ml (0.1 to 1 liters). Clinical doses for most purposes are expected to be in the range from about 200 to 500 ml (0.2 to 0.5 liters).

Ultrasonic imaging and development of the echocardiogram can be carried out by standard procedures using commercially available equipment. For use with the dispersion of this invention, the frequency of the ultrasonic beam can be varied for example, from 1 to 10 MHz. For imaging of the GI tract, it is believed that effective enhancement can be obtained in the range from 2 to 6 MHz, which corresponds with typical frequencies for abdominal examinations (e.g. 3 to 5 Mhz).

The imaging agent may be administered orally for examination of the stomach, the upper portions of the small intestines, including the duodenum and jejunum. Rectal administration can be used for examining sections of the large intestines. The imaging may be carried out as soon as the imaging agent has reached the section of the GI tract to be examined. However, the imaging may sometimes be delayed, such as where it is desired to carry out the examination with the imaging agent as a coating rather than as a liquid volume in the section to be examined. It is believed that useful examinations can be made in a short as time as five minutes and up to 120 minutes. However, most examinations will probably be carried out at about 10 to 30 minutes after the administration of the imaging agent.

For certain purposes, the imaging agent may be used to displace the air in the stomach, or sections of the colon. Large air volumes can substantially block ultrasonic wave transmission When the imaging agent replaces the air in a cavity, such as the stomach, increased penetration of the ultrasound waves can be obtained, thereby making it possible to, in effect, see through the stomach or another organ. For example, this technique may be used to improve ultrasonic examinations of the pancreas.

The method of this invention and the results that can be obtained thereby are further illustrated in the following experimental examples.

EXAMPLE I

A series of experimental tests were carried out according to the following procedure:

A. Data Acquisition

Several hours before the experiment is performed, a 20 liter reservoir is filled with tap water that has passed through a $0.3\mu$ filter (Millipore Model 12116), allowing the water to equilibrate to room temperature. During the experiment, the water flows through 7/16" O.D., 5/16" I.D. latex tubing at a rate of 500 ml/min as a result of a Materflex Model 7524-00 pump. The pulsatile pump is followed by a surge suppressor (Model 7596-20 pump) to lessen the fluctuations of the flow rate away from 500 ml/min. Finally, the fluid flows through a RMI Tissue Mimicking Ultrasound Phantom (Model 409A, $\alpha=0.5$ Db/cm/Mhz, c=1540 m/s). The volume of the tube inside the phantom is 10 ml.

The GI contrast agents were, in general, prepared according to the following method. A 2.54% (w/v) solution of the agent is prepared in water. The solution is mixed in a Waring blender for 20 seconds, followed by degassing for 20 minutes. Into a 3 ml syringe fitted with an 18 gauge metal needle is withdrawn 1 ml of the sample at a rate of 0.5 ml/sec and this is injected into the flow stream at the rate of 1 ml/sec. The injection site is 70 cm in front of the phantom. The solution to be injected is further diluted by the fluid flowing in the tubing of the phantom; this factor give a dilution of 8.3.

A Hewlett-Packard Sonos 100 Ultrasound Imaging system with a 3 Mhz transducer (focal zone=4-6 cm) is used in B mode to detect the scattering capability of the sample solution. The transmit, compression, and time-gain compensation controls of the ultrasound system are adjusted until an image sector of the phantom is judged visually to be optimal. The entire injection sequence (before, during and after) is recorded on videotape (attached to the ultrasound system) for storage and analysis.

B. Data Analysis

The injection sequence is then digitized onto an Apple Macintosh II computer using CineProbe image processing software. A Region of Interest (ROI) is identified within the image sector to include the region within the phantom tubing to be examined. This region is an area 80 pixels wide by 160 pixels high, representing a volume within the tube of the flow phantom of 0.45 ml. With the videotape machine in the play mode, the regions of interest are digitized at a rate of 20 frames/- sec. This process continues until the entire injection sequence has been digitized, resulting in 200 frames.

Each frame within the series of frames is then analyzed as to its video density within the flow tube of the phantom. Within each frame, 1800 pixels are analyzed, equivalent to 31% of the imaged tube and 6% of the total tube within the phantom. The videodensity of the 1800 pixels are averaged, resulting in the videodensity of that frame.

The total backscatter during the experiment that results from the presence of the sample GI agent is measured by the area of the time-videodensity curve above the baseline.

Using the foregoing procedures for data acquisition and data analysis, a series of water-insoluble cereal brans were compared. The results are summarized below in Table A.

TABLE A
Study of Fibrous Vegetable Particles

| Sample | Area (pixels × seconds) | Particle Size (microns) |
|---|---|---|
| Corn Bran | 921 | (10 × 20)–(250–350) |
| Oat Bran | 2346 | <60 |
| Rice Bran | 2288 | (30 × 30)–(200 × 300) |
| Wheat Bran | 5220 | (50 × 50)–(250 × 350) |
| Wheat Bran Flakes | 4454 | (40 × 40)–(350 × 350) |

EXAMPLE II

Using the data acquisition and data analysis procedures of Example I, a series of hydrocolloid particles was prepared and tested. The results are summarized below in Table B.

TABLE B
Hydrocolloid Particles

| Sample | Area (pixels × seconds) | Particle Size (microns) |
|---|---|---|
| Gum Ghatti | 746 | <60 |
| Gum Guar | 3746 | <30 |
| Gum Locust Bean | 2500 | 10–100 |
| Gum Tragacanth | 3498 | <20 |
| Gum Xanthan | 2954 | <30 |
| Pectin | 1987 | <20 |
| Carageenan (Type 1) | 1763 | 120 |
| Carageenan (Type 2) | 4110 | 300 |
| Bacto Agar | 2911 | <30 |
| Agar Agar | 2249 | <50 |
| Agar Seaweed | 3133 | <30 |

EXAMPLE III

Using the data acquisition and data analysis procedures of Example I, a series of commercial diet drink products were prepared and tested. These products contained bran and hydrocolloids, and other ingredients as shown in Table C, below, which summarizes the data.

TABLE C
Commercial Diet Drink Products
(Containing Insoluble Particles and Hydrocolloids)

| Product | Area (pixels × seconds) |
|---|---|
| Dynatrim[a] | 5442 |
| Cal. Slim[b] | 3030 |
| Ultra Slim Fast[c] | 1029 |
| Slim Fast[d] | 619 |
| Bahamian Diet[e] | 896 |

[a]Dynatrim is the trademark name of a dietary drink product sold by Lederley Laboratories, Pearl River, New York. It contains a mixture of oat bran and corn bran together with a plurality of hydrocolloids (cellulose gum, gum arabic, carboxymethylcellulose, pectin, and guar gum). As tested, 2.54 g of Dynatrim were dispersed per 100 ml water.
[b]California Slim is a trademark name of a dietary drink produced marketed by California Slim, Inc., La Jolla, California. It contains a mixture of oat bran and rice bran together with guar gum and cellulose. It was tested at the concentration shown in Footnote [a].
[c]Ultra Slim Fast is a trademark name of a dietary drink mix sold by the Nutrition Division of Thompson Medical Co., New York, New York. It contains corn bran together with purified cellulose and hydrocolloids (cellulose gum, guar gum and carageenan). It was tested at the concentration shown in Footnote [a].
[d]Slim Fast is a trademark name of a dietary drink mix sold by the Nutrition Division of Thompson Medical Co., New York, New York. It contains a mixture of purified cellulose and bran fiber together with carageenan. It was tested at the concentration shown in Footnote [a].
[e]This product is a dietary drink mix sold under the name "Dick Gregory's Slim Safe Bahamian Diet", by Correction Connection, Inc., Philadelphia, PA. It contains cellulose powder in admixture with rice bran, wheat germ, wheat grass and dolomite together with hydrocolloids (guar gum, pectin, xanthan gum, and carageenan). It was tested at the concentration shown in Footnote [a].

EXAMPLE IV

Following the procedures of Example I with respect to data acquisition and data analysis, a series of mixtures of bran and hydrocolloids were prepared and tested. The results are summarized below in Table D, the footnotes of which provide further details with respect to the mixtures tested.

TABLE D
Formulations of Insoluble Particles and Hydrocolloids

| | Measured[1] | Estimated[2] |
|---|---|---|
| 100% Gum Tragacanth | 100 | |
| 100% Bacto Agar | 210 | |
| 50% Gum Tragacanth + 50% Bacto Agar | 207 | 155 (50 + 105) |
| 100% Gum Tragacanth | 100 | |
| 100% Wheat Bran | 24 | |
| 50% Gum Tragacanth + 50% Bacto Agar | 167 | 62 (50 + 12) |
| 100% Gum Tragacanth | 100 | |
| 100% Cellulose | 5 | |
| 50% Gum Tragacanth + 50% Bacto Agar | 92 | 52 (50 + 2) |

[1]Integrated Area measurements normalized to values of Gum Tragacanth (pixels × seconds).
[2]Estimated from separate measurements on a presumed additive basis.

We claim:

1. The method of ultrasound imaging of the gastrointestinal (GI) tract wherein the improvement comprises: introducing into the portion of the GI tract to be examined an aqueous dispersion containing from 0.5% to 10% by weight particulate solids sized in the range from 1 to 500 microns, said solids being selected from the group consisting of insoluble fibrous vegetable particles, insoluble mineral particles, hydrocolloid particles, and mixtures thereof, and applying an ultrasonic imaging beam to said GI tract portion for imaging thereof, the concentration of said particles in said dispersion being effective to enhance the contrast of the image obtained.

2. The method of claim 1 in which said dispersion contains a mixture of said fibrous vegetable particles and said hydrocolloid particles, and said fibrous vegetable particles are selected from the group consisting of cereal grain brans, cellulose, and mixtures thereof.

3. The method of claim 1 in which said dispersion contains from 2 to 8% particulate solids by weight.

4. The method of claim 2 in which said dispersion contains by weight from 2 to 6% bran particles and from 0.5 to 4% hydrocolloid particles.

5. The method of ultrasound imaging of the gastrointestinal (GI) tract wherein the improvement comprises: introducing into the portion of the GI tract to be examined an aqueous dispersion containing from 2 to 8% by weight particulate solids sized in the range from 10 to 300 microns, said solids being selected from the group consisting of insoluble bran particles, hydrocolloid particles, and mixtures thereof, and applying an ultrasonic imaging beam to said GI tract portion for imaging thereof, the concentration of said particles in said dispersion being effective to enhance the image obtained.

6. The method of claim 5 in which said dispersion contains a mixture of said bran particles and said hydrocolloid particles.

7. The method of claim 6 in which said dispersion contains by weight from 2 to 6% of said bran particles and from 0.5 to 4% of said hydrocolloid particles.

8. The method of claims 4, 5, 6, or 7, in which said bran is selected from the group consisting of corn bran, oat bran, rice bran, wheat bran and mixtures thereof.

9. The method of claims 4, 5, 6, or 7, in which said hydrocolloid is a natural hydrocolloid selected from the group consisting of gum ghatti, gum guar, locust bean gum, tragacanth gum, xanthan gum, pectin, carageenan, agar, and mixtures thereof.

10. The method of ultrasound imaging of the gastrointestinal (GI) tract wherein the improvement comprises: introducing into the portion of the GI tract to be examined an aqueous dispersion containing from 2 to 8% by weight particulate solids sized in the range from 10 to 300 microns, said solids comprising a mixture of insoluble bran particles and hydrocolloid particles, from 2 to 6% by weight said bran particles being present in admixture with from 0.5 to 4% hydrocolloid particles, said bran particles being selected from the group consisting of corn bran, oat bran, rice bran, wheat bran and mixtures thereof, and said hydrocolloid particles being selected from the group consisting of gum ghatti, gum guar, locust bean gum, tragacanth gum, xanthan gum, pectin, carageenan, agar, and mixtures thereof, and applying an ultrasonic imaging beam to said GI tract portion for imaging thereof, the concentration of said particles in said dispersion being effective to enhance the contrast of the image obtained.

11. The method of ultrasound imaging of the gastrointestinal (GI) tract wherein the improvement comprises: introducing into the portion of the GI tract to be examined an aqueous dispersion containing from 0.5% to 10% by weight particulate solids sized in the range from 1 to 500 microns, said solids comprising the combination of partially swollen hydrocolloid particles with non-swelling insoluble particles selected from the group consisting of fibrous vegetable particles, inorganic mineral particles, and mixtures thereof, and applying an ultrasonic imaging beam to said GI tract portion for imaging thereof, the concentration of said particles in said dispersion being effective to enhance the contrast of the image obtained.

12. The method of claim 11 in which said fibrous vegetable particles are selected from the group consisting of brans and cellulose.

13. The method of claim 11 or 12 in which said hydrocolloid particles are a natural vegetable gum.

14. The method of claim 11 in which said fibrous vegetable particles are bran particles selected from the group consisting of corn bran, oat bran, rice bran, wheat bran and mixtures thereof.

15. The method of claim 11 in which said hydrocolloid particles are selected from the group consisting of gum ghatti, gum guar, locust bean gum, tragacanth gum, xanthan gum, pectin, carageenan, agar, and mixtures thereof.

* * * * *